United States Patent [19]

Fleming et al.

[11] Patent Number: 5,149,603
[45] Date of Patent: Sep. 22, 1992

[54] BATTERY PACK FOR MEDICAL INSTRUMENTS

[75] Inventors: Thomas W. Fleming, Van Nuys; Lanny A. Gorton, Sunland; Paul S. Cheney, II, Canyon Country, all of Calif.

[73] Assignee: Pacesetter Infusion, Lts., Sylmar, Calif.

[21] Appl. No.: 636,042

[22] Filed: Dec. 27, 1990

[51] Int. Cl.$^5$ .............................................. H01M 2/10
[52] U.S. Cl. ......................................... 429/98; 429/65; 429/97; 429/99; 429/100; 429/123; 429/177; 429/185; 429/186; 128/419 R; 606/32
[58] Field of Search ...................... 429/96, 97, 98, 65, 429/99, 100, 123, 177, 185, 186; 606/1, 32; 128/419 R

[56] References Cited

U.S. PATENT DOCUMENTS

| | | | |
|---|---|---|---|
| 4,288,733 | 9/1981 | Bilanceri et al. | 429/163 |
| 4,294,891 | 10/1981 | Yao et al. | 429/2 |
| 4,389,469 | 6/1983 | Nicholls | 429/100 |
| 4,608,528 | 8/1986 | Stilwell | 429/100 |
| 4,806,440 | 2/1989 | Halts, Jr. et al. | 429/97 |
| 4,880,713 | 11/1989 | Levine | 429/96 |
| 4,957,829 | 9/1990 | Holl | 429/186 |
| 5,004,129 | 4/1991 | Loch et al. | 429/97 |
| 5,021,305 | 6/1991 | Turner | 429/65 |

Primary Examiner—McFarlane Anthony
Attorney, Agent, or Firm—Leslie S. Miller

[57] ABSTRACT

An improved battery pack is provided for short term battery power operation of a medical instrument such as an infusion pump. The battery pack comprises a substantially closed and compact housing one or more rechargeable batteries inaccessibly encased therein, with the battery pack housing being adapted for mounting directly onto the casing of an electronic medical instrument. The batteries are mounted on a base plate beneath a foil shield and a housing cap, both of which are attached to the base plate in a manner precluding nondestructive removal thereof and thereby substantially preventing access to the batteries. The assembled battery pack housing includes seal members for preventing passage of any gases discharged from the batteries into the medical instrument casing, and further defines at least one vent for exhaust passage of such gases to the exterior of the battery pack and medical instrument.

27 Claims, 3 Drawing Sheets

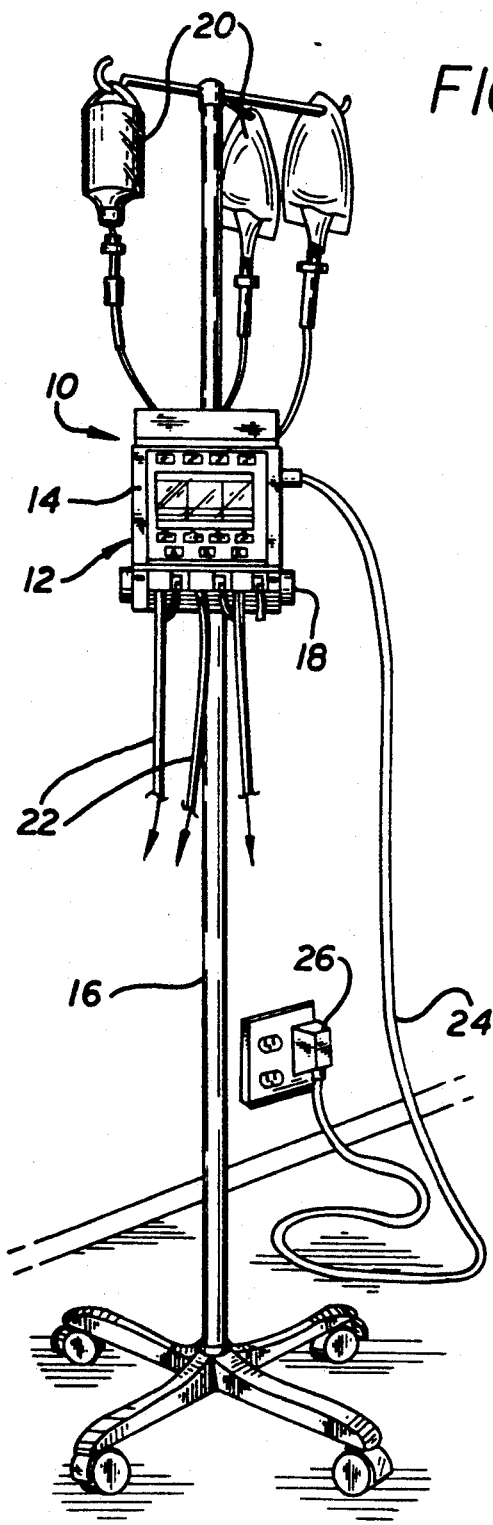
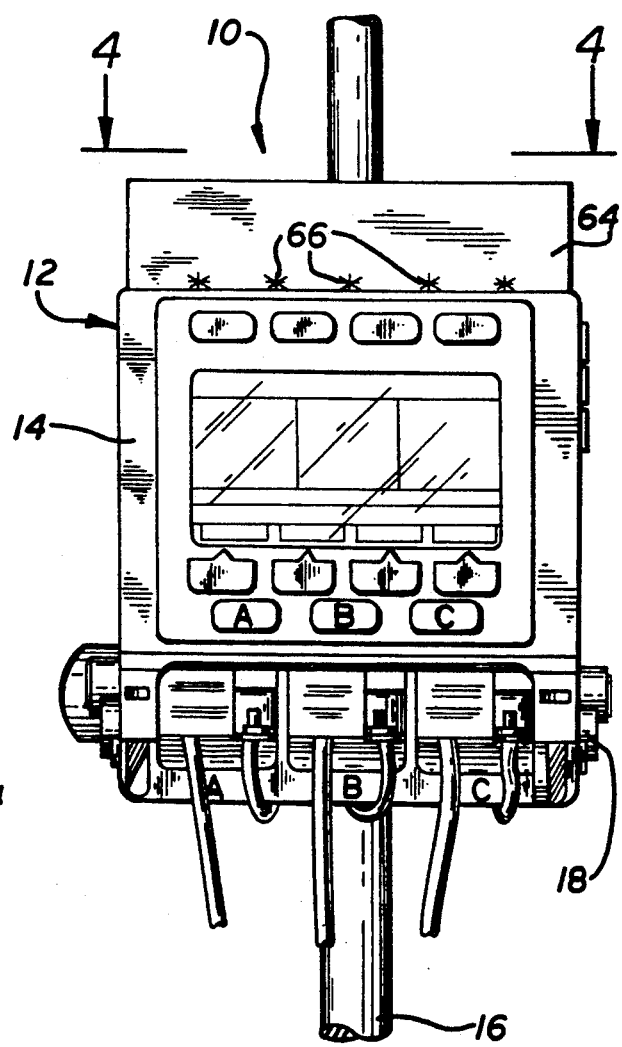
FIG. 1
FIG. 2

BATTERY PACK FOR MEDICAL INSTRUMENTS

BACKGROUND OF THE INVENTION

This invention relates generally to an improved battery pack for use in short term battery powered operation of a medical instrument, such as an infusion pump of the type used to deliver selected fluids to a patient according to a prescribed time schedule. More particularly, this invention relates to a compact battery pack having one or more rechargeable batteries mounted permanently and substantially inaccessibly therein.

Modern medical treatment facilities utilize a variety of relatively sophisticated electronic instruments in the course of patient diagnosis and treatment. As one common example, electronic fluid infusion instruments are commonly used for administering one or more selected medical fluids to a patient at a prescribed flow rate and time schedule. Such fluid infusion and other electronic equipment require a source of electrical power to maintain the medical instrument in a desired operational state. In this regard, such medical instruments are normally designed to operate on conventional 120 volt AC power and include appropriate power cords for plug-in connection to a standard household power supply.

Alternatively, in some cases, the medical instrument is designed to operate on a DC power supply which is obtained by connecting an appropriate transformer to a standard household power supply. In this latter case, medical instruments have been provided with internal transformers integrated directly into the instrument housing, or an external transformer adapted for direct plug-in connection to a power supply outlet.

While electrically-powered medical instruments have significantly enhanced medical diagnosis and treatment, it is often necessary for an electronic instrument to be disconnected from its regular power source to permit patient and/or instrument movement from one location to another within a medical facility. In this regard, some medical instruments have been designed for relatively short term battery operation to accommodate continuous instrument operation as the patient and instrument are moved.

In such devices, the battery power source has normally been integrated directly into the housing of the medical instrument, frequently in association with an on-board charger designed to maintain the battery source in a recharged state when the instrument is connected to the normal AC power supply. However, such arrangements have not safeguarded against unauthorized replacement of the battery source with cheaper and potentially inferior batteries. Moreover, such prior arrangements have not effectively isolated the electronic components of the medical instrument from potentially explosive gases which are sometimes generated in the event of battery malfunction.

There exists, therefore, a significant need for improvements in integrating a battery power source with a medical instrument for short term instrument operation, particularly wherein the battery source is easily accessed for replacement with fresh batteries, when necessary. Moreover, there exists a need for providing a high quality battery power source wherein the use of potentially inferior batteries is effectively prevented. Still further, there exists a need for providing a short term battery power source in a medical instrument, wherein the battery source is effectively isolated from electronic components of the medical instrument. The present invention fulfills these needs and provides further related advantages.

SUMMARY OF THE INVENTION

In accordance with the invention, an improved battery pack is provided for short term battery powered operation of a medical instrument such as an infusion pump or the like. The battery pack includes a compact battery pack housing having one or more rechargeable batteries mounted inaccessibly therein. The battery pack housing is adapted for relatively quick and easy mounting directly onto an associated medical instrument, and for simple connection of the rechargeable batteries to electronic components within the medical instrument. The inaccessible mounting of the batteries prevents tampering therewith and/or replacement thereof with potentially inferior batteries.

In the preferred form of the invention, one or more rechargeable batteries are mounted securely onto a base plate. Conductors are appropriately connected to the batteries and are passed through a sealing grommet to a suitable connector adapted for mating with a mating connector within the medical instrument. A foil shield is mounted onto the base plate in a position covering the batteries, and in a permanent manner to prevent foil shield removal without destruction thereof.

A housing cap is in turn mounted onto the base plate in a position covering the foil shield, and in a permanent manner to prevent cap and base plate separation without destruction of the battery pack housing. The thus-assembled battery pack housing is sized and shaped for relatively simple yet secure mounting onto the medical instrument, such as by means of a plurality of screws passed through open ports in the battery pack housing and fastened into the casing of the medical instrument.

The screw ports formed in the battery pack housing incorporate seal members such as O-rings which cooperate with the sealing grommet to isolate the rechargeable batteries from electronic components within the interior of the medical instrument. Accordingly, any gases discharged by the batteries upon potential malfunction thereof are isolated from the medical instrument and its electronic components. Such gases are vented between the base plate and housing cap through one or more open vents to the exterior of the medical instrument.

In addition in accordance with further aspects of the invention, the foil shield comprises a paper-based shell having a thin film conductive foil applied thereto. This paper-based shell includes apertured tabs to fit over short upstanding posts on the base plate, after which the posts are deformed as by heat staking to permanently affix the foil shield onto the base plate. The tabs of the foil shield are folded over to provide a continuous conductive path associated with metalized shielding normally integrated into the medical instrument.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which:

FIG. 1 is a perspective view illustrating a medical instrument in combination with the improved battery pack embodying the novel features of the invention;

FIG. 2 is an enlarged fragmented front elevation view depicting the medical instrument and associated battery pack of FIG. 1;

DETAILED DESCRIPTION OF THE PREFERRED EMBODIMENT

Figure 3:
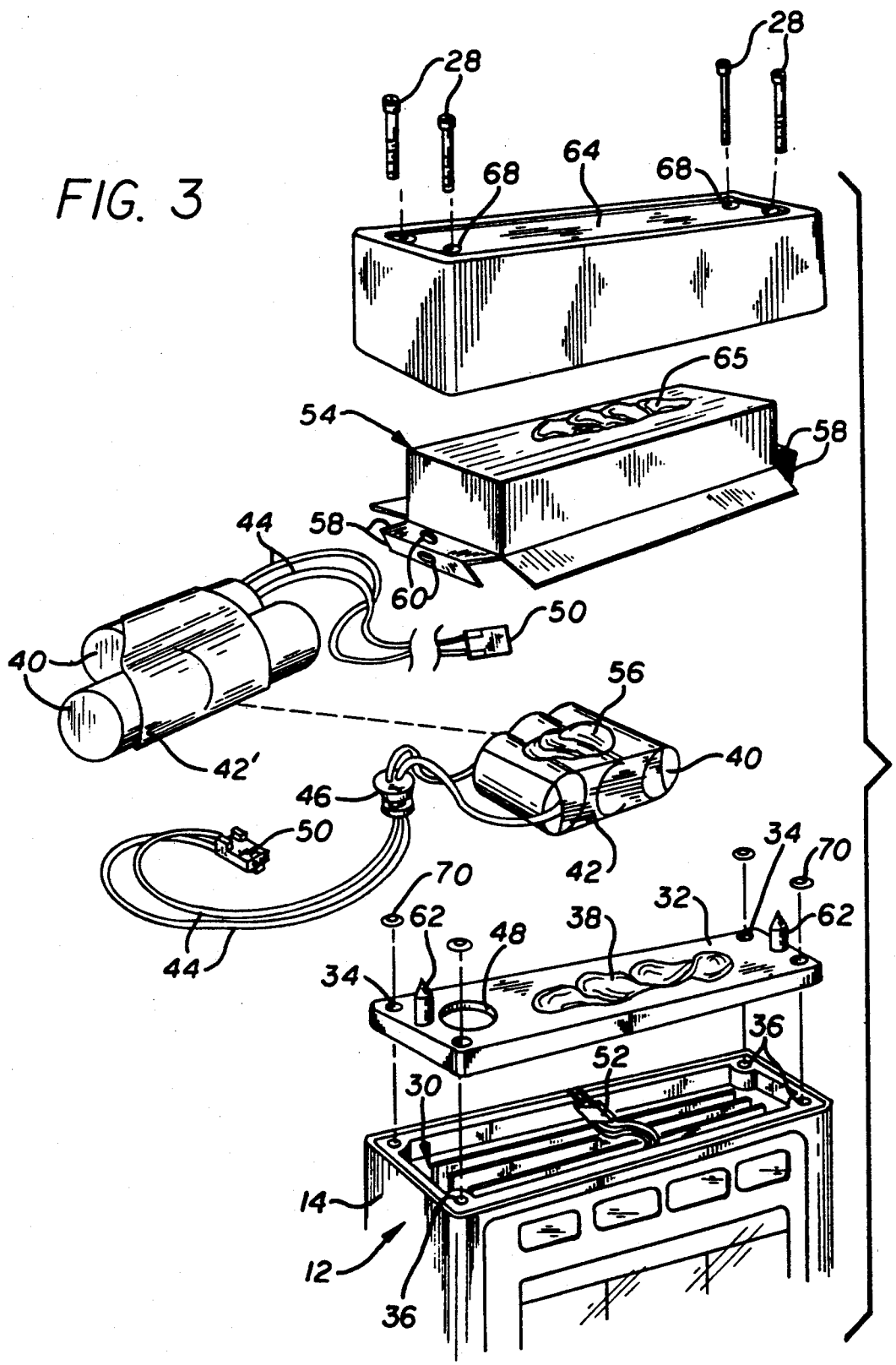
FIG. 3 is a further enlarged and exploded perspective view illustrating assembly of battery pack components and mounting thereof onto the associated medical instrument.
Figure 4:
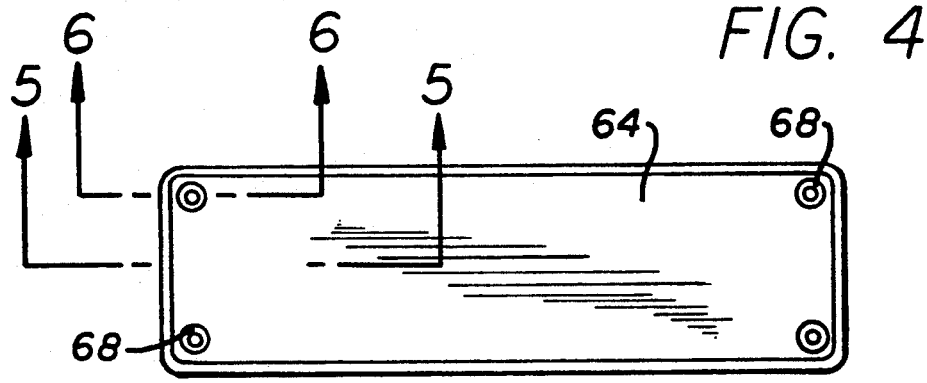
FIG. 4 is a top plan view taken generally on the line 4—4 of FIG. 2.

As shown in the exemplary drawings an improved battery pack referred to generally in FIGS. 1 and 2 by the reference numeral 10 is provided for alternative short term battery powered operation of a medical instrument 12, such as the illustrative medication infusion pump of a type used to administer one or more medical fluids to a patient in a regulated manner.

The battery pack 10 is designed for quick and easy mounting directly onto the associated medical instrument 12, with the battery pack 10 providing a convenient alternative power source for uninterrupted instrument operation while permitting transport of the instrument 12 and associated patient (not shown) from one place to another. The battery pack 10 provides these advantages while substantially precluding access to a battery power source, thereby preventing unauthorized tampering with or replacement of the battery power source with potentially inferior components.

Although the battery pack 10 of the present invention may be designed for use with a wide range of electronic medical instruments, the illustrative drawings show the battery pack 10 in association with a fluid medication infusion pump 12 such as the MiniMed III fluid infusion pump marketed by MiniMed Technologies of Sylmar, Calif., which infusion pump shall also be referred to by the reference numeral 12. More particularly, the illustrative infusion pump 12 comprises a relatively compact instrument casing 14 adapted for mounting onto a conventional portable medical equipment pole 16 by means of an appropriate adjustable clamp bracket 18 or the like.

The infusion pump 12 includes multiple parallel pumping systems for independent programming control to regulate administration of multiple medical fluids from appropriate reservoirs 20 to the patient (not shown) via suitable tubing 22. Electronic control components and associated mechanical pumping devices are integrated into the instrument casing 14. The infusion pump 12 is designed for normal operation by connection to an appropriate 120 volt AC power supply, as by means of a power cord 24 and associated plug-in transformer 26 as viewed in FIG. 1. The battery pack 10 provides for several hours of continuous instrument operation when the transformer 26 is unplugged from the normal power supply.

As shown best in FIGS. 1-3, the battery pack 10 of the present invention is adapted for mounting directly onto the top of the casing 14 of the infusion pump 12. More particularly, a plurality of mounting screws 28 (FIG. 3) are normally provided with the instrument to attach a cover plate (not shown) directly onto the top of the instrument casing 14. This cover plate normally encloses the top of the instrument casing and thereby prevents access to internal electronic and other components referenced generally in FIG. 3 by the reference numeral 30.

The battery pack 10 is mounted onto the top of the infusion pump 12 by removing the normal cover plate, and by utilizing the mounting screws 28 to install the battery pack 10 directly over the top of the instrument casing 14.

The battery pack 10 comprises a base plate 32 which is the preferred form constructed from a lightweight molded plastic material. The base plate 32 has a plurality of screw ports 34 formed therein for respective passage of the mounting screws 28 into threaded receptacles 36 formed as part of the instrument casing 14. A suitable adhesive 38 or the like is applied to an upper central region of the base plate 32 for securely and permanently attaching one or more rechargeable batteries 40 directly onto the base plate.

As shown in FIG. 3 the batteries 40 are typically grouped in an appropriate plurality according to the DC operating requirements of the medical instrument, with appropriate plastic casings 42 or 42' alternatively being used to capture the batteries 40 as a unit for secure mounting onto the base plate 32. Electrical conductors 44 are appropriately connected to the batteries 40 and passed through a sealing grommet 46 adapted for press-fit installation into an open port 48 formed in the base plate 32. The battery conductors 44 terminate in a suitable connector 50 adapted for mating plug-fit connection with a counterpart connector 52 within the instrument casing 14.

A foil shield 54 is integrated into the battery pack 10 for shielding the upper region of the infusion pump 12. The illustrative foil shield 54 comprises a folded box of downwardly open geometry formed preferably from a lightweight paper base with a thin metalized film of aluminum or the like applied thereto. The foil shield 54 is preferably securely fastened over the batteries 40 by means of additional adhesive 56. In addition, the foil shield 54 includes a pair of tabs 58 each folded over upon itself and including suitable apertures 60 to fit over stake posts 62 upstanding from the base plate 32.

Figure 5:
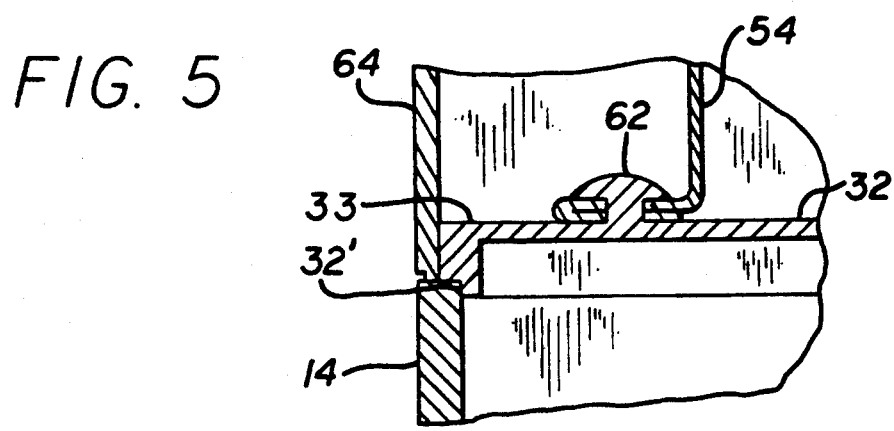
FIG. 5 is an enlarged fragmented vertical sectional view taken generally on the line 5—5 of FIG. 4.

As shown in FIG. 5, the stake posts 62 are deformed as by application of heat or the like subsequent to foil shield mounting to permanently affix the foil shield 54 in position over the rechargeable batteries 40. With this construction, the batteries 40 are rendered substantially inaccessible without destroying the foil shield 54.

A downwardly open housing cap 64 (FIGS. 4-7) of molded plastic or the like is then mounted on the base plate 32 in a position overlying the foil shield 54 and batteries 40. A preferred mounting arrangement utilizes a spaced plurality of ultrasonic spot welds 66 (FIG. 2) for interconnecting a lower margin of the cap 64 to the outer periphery of the base plate 32. With this arrangement, the assembled cap 64 and base plate 32 are effectively vented to permit escape of any toxic or hazardous gases which might be generated by the batteries 40 in the event of battery malfunction. Additional adhesive 65 may also be used to permanently attach the batteries 40 via the foil shield 54 to the cap 64.

Figure 6:
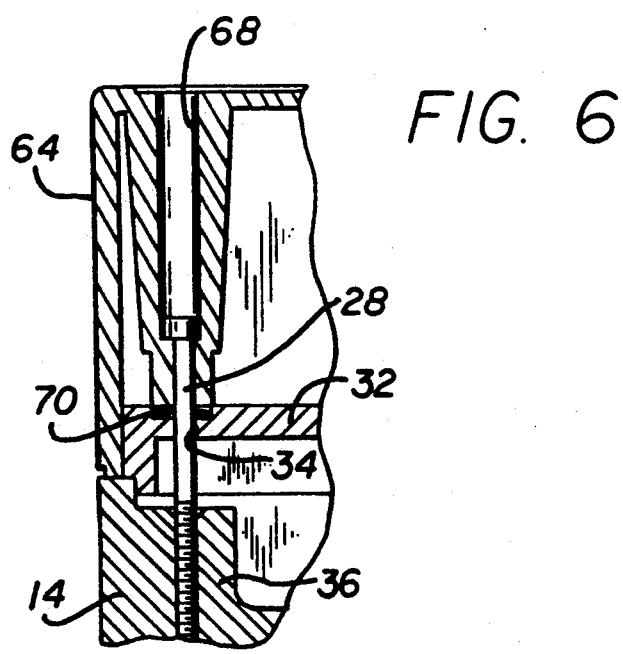
FIG. 6 is an enlarged fragmented vertical sectional view taken generally on the line 6—6 of FIG. 4.

The mounting screws 28 are passed through aligned screw ports 68 in the housing cap 64 and further through the screw ports 34 in the base plate 32 for threaded reception into the instrument casing receptacles 36. As shown in FIG. 6, the base plate ports 34 receive seal members such as O-rings 70 held tightly against the base plate by cap cylinders 72 when the mounting screws 28 are installed. With this geometry, the underlying interior of the instrument casing 14 is effectively isolated from the batteries 40 within the battery pack 10, by virtue of the sealing action of the seal rings 70 and the sealing grommet 46.

As noted above, any hazardous gases generated by the batteries are vented to the exterior of the instrument, and are not permitted to pass through the base plate 32 into association with electronic components within the instrument casing 14.

According to further aspects of the invention, the folded end tabs 58 on the foil shield 54 beneficially provide a continuous conductive path between the exterior of the foil shield 54 and the base plate 32. In this regard, with reference to FIG. 5, selected regions of the base plate 32 including at least the zone between the stake posts 62 and a side edge 32' incorporate a thin metalized conductive film 33 for continuity of the conductive shield to the instrument casing 14 when the battery pack 10 is assembled therewith. In other words, the foil shield 54 cooperates with the base plate 32 and the underlying casing 14 to provide a continuous shielding of the entire battery pack and instrument, thereby improving instrument performance and reliability.

The battery pack 10 of the present invention is thus adapted for rapid mounting directly onto an associated medical instrument, and for rapid connection directly to electronic components 30 within the instrument casing 14. During normal instrument operation by connection to a standard AC power supply, the electronic components 30 of the instrument may be adapted for maintaining the batteries 40 in a fully charged state. In the illustrative embodiment which utilizes the plug-in transformer 26 at an AC wall outlet, such charging of the batteries may be accomplished without requiring an internal battery charger within the instrument casing 14.

Instead, battery charging can take place by merely connecting the appropriate DC signal across the batteries 40 for charging purposes. However, when the power cord 24 is disconnected from the instrument casing 14, the electronic components 30 respond automatically to connect the batteries 40 to the instrument in a manner maintaining continuity of instrument operation. In this regard, although various battery types can be used, rechargeable nickel cadmium batteries are preferred for providing several hours of continuous operation for the medical instrument.

Importantly, while the battery pack 10 provides for rapid battery pack mounting and/or replacement as may be periodically required, the batteries 40 are substantially inaccessible at all times. That is, the housing cap 64 and the foil shield 54 cannot be removed from the underlying base plate 32 to expose the batteries, without substantially destroying the battery pack in a readily visible manner. With this construction, the integrity of the rechargeable batteries 40 is maintained, so that the correct batteries associated with the particular instrument cannot be tampered with or otherwise replaced with potentially inferior batteries which might have an adverse impact upon instrument operation.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A battery pack for battery powered operation of an electronic medical instrument, said battery pack comprising:
   a base plate;
   at least one battery mounted on said base plate;
   a foil shield mounted onto said base plate in a position covering said at least one battery;
   a housing cap;
   means for mounting said housing cap onto said base plate, said housing cap cooperating with said base plate to enclose said at least one battery and said foil shield and to prevent access to said at least one battery without at least partial destruction of one of said housing cap and base plate; and
   conductor means for connecting said at least one battery to the medical instrument.

2. A battery pack as defined in claim 1, further comprising:
   means for mounting said foil shield onto said base plate, said foil shield and said base plate cooperating to enclose said at least one battery and to prevent access thereto without at least partial destruction of one of said foil shield and base plate.

3. A battery pack as defined in claim 1, wherein said at least one battery comprises:
   at least one rechargeable battery.

4. A battery pack as defined in claim wherein said base plate has an open port formed therein, said conductor means extending through said open port for connecting said at least one battery to the medical instrument, and further comprising a sealing grommet for sealing passage of said conductor means through said open port.

5. A battery pack as defined in claim 1, further comprising:
   means for mounting said base plate onto the medical instrument.

6. A battery pack as defined in claim 5, wherein said means for mounting said battery pack onto the medical instrument comprises:
   means for isolating the medical instrument from gases discharged from said at least one battery.

7. A battery pack as defined in claim 6, wherein said means for mounting said battery pack onto the medical instrument comprises:
   at least one screw extending through a screw port formed in said battery pack and fastened into the medical instrument, said isolating means comprising a seal ring lining said screw port.

8. A battery pack as defined in claim 7, wherein said base plate has an open port formed therein, said conductor means extending through said open port for connecting said at least one battery to the medical instrument, and further comprising a sealing grommet for sealing passage of said conductor means through said open port.

9. A battery pack as defined in claim 1, further including adhesive means for mounting said at least one battery onto said base plate.

10. A battery pack as defined in claim 1, further comprising:

adhesive means for mounting said foil shield onto said at least one battery.

11. A battery pack as defined in claim 2, wherein said foil shield mounting means comprises:
   a pair of apertured tabs on said foil shield for receiving a respective pair of stake posts on said base plate, said stake posts being deformable subsequent to reception of said tabs to permanently attach said tabs to said base plate.

12. A battery pack as defined in claim 11, wherein said foil shield comprises:
   a paper based shell with a conductive film thereon, said tabs of said foil shield being folded over such that said conductive film contacts said base plate when said foil shield is mounted onto said base plate.

13. A battery pack as defined in claim 12, further comprising:
   means for mounting said battery pack onto the medical instrument, said base plate including metalized film for conductively connecting said foil shield to the medical instrument when said battery pack is mounted onto the medical instrument.

14. A battery pack as defined in claim 1, wherein said means for mounting said housing cap onto said base plate defines at least one vent for venting gases discharged from said at least one battery.

15. A battery pack for battery powered operation of an electronic medical instrument, said battery pack comprising:
   a least one battery;
   a battery pack housing including first and second housing members connected to each other to enclose said at least one battery and to prevent access to said least one battery without at least partial destruction of said housing;
   conductor means for connecting said at least one battery to the medical instrument, said conductor means extending from within said housing through an open port formed therein to the exterior of said housing; and
   means for sealing passage of said conductor means through said open port.

16. A battery pack as defined in claim 15, further comprising:
   means for mounting said housing onto the medical instrument, said housing defining at least one vent for venting gas discharged from said at least one battery to the exterior of said housing.

17. A battery pack as defined in claim 16, wherein said first and second housing members are interconnected by a plurality of spaced-apart welds.

18. A battery pack as defined in claim 15, further comprising:
   a foil shield mounted onto one of said first and second housing members and cooperating therewith to enclose said at least one battery and to prevent access to said at least one battery without at least partial destruction of one of said foil shield and said one housing member.

19. A battery pack in combination with a medical instrument having an open-ended casing with electronic components therein, said battery pack for battery powered operation of said medical instrument, said battery pack comprising;
   a base plate having an open port formed therein and adapted for mounting onto said instrument casing to extend over and generally cover the open end of said casing;
   at least one battery mounted on said base plate on one side of said base plate opposite said casing;
   conductor means for connecting said at least one battery to said instrument, said conductor means extending through said open port in said base plate and including a first fitting for connection with a second fitting disposed within said casing;
   a seal member for sealing passage of said conductor means through said open port formed in said base plate;
   a foil shield mounted on said base plate and cooperating therewith to enclose said at least one battery and to prevent access thereto without at least partial destruction of one of said shield and said base plate;
   a housing cap mounted on said base plate and cooperating therewith to enclose said at least one battery and said foil shield and to prevent access thereto without at least partial destruction of one of said cap and said base plate; and
   means for mounting said base plate onto said casing to extend over and generally cover the open end of said casing.

20. A combination as defined in claim 19, wherein said means for mounting said base plate onto said casing comprises:
   at least one screw passed through aligned screw ports formed in said cap and said base plate, said screw being fastened into a threaded receptacle on said casing, and further comprising a seal ring seated within the screw port formed in said base plate.

21. A combination as defined in claim 19, further comprising:
   adhesive means for mounting said at least one battery onto said base plate.

22. A combination as defined in claim 19, further comprising:
   adhesive means for mounting said foil shield onto said at least one battery.

23. A combination as defined in claim 19, wherein said foil shield comprises:
   a pair of apertured tabs for receiving a respective pair of stake posts formed on said base plate, said stake posts being deformable subsequent to reception of said tabs to permanently attach said tabs to said base plate.

24. A combination as defined in claim 23, wherein said foil shield comprises:
   a paper based shell with a conductive film thereon, said tabs of said foil shield being folded over such that said conductive film contacts said base plate when said foil shield is mounted onto said base plate.

25. A combination as defined in claim 24, wherein said base plate comprises:
   metalized film for conductively connecting said foil shield to said casing.

26. A combination as defined in claim 24, wherein said housing cap and said base plate cooperatively define at least one vent for venting gas discharged from said at least one battery to the exterior of said battery pack and said instrument casing.

27. A method of making a battery pack for battery powered operation of an electronic medical instrument, said method comprising:
   mounting at least one battery on a base plate;

mounting a foil shield onto said base plate in a position covering said at least one battery;

mounting a housing cap onto said base plate, said housing cap cooperating with said base plate to enclose said at least one battery and said foil shield and to prevent access to said at least one battery without at least partial destruction of one of said housing cap and base plate; and connecting conductor means to said at least one battery, said conductor means for use to supply power to the medical instrument.

* * * * *

UNITED STATES PATENT AND TRADEMARK OFFICE
CERTIFICATE OF CORRECTION

PATENT NO. : 5,149,603
DATED : September 22, 1992
INVENTOR(S) : Thomas W. Fleming, Lanny A. Gorton and Paul S. Cheney, II It is certified that error appears in the above-indentified patent and that said Letters Patent is hereby corrected as shown below:

Column 6, Claim 4, Line 34, after "claim", add --1,--.

Signed and Sealed this

Thirteenth Day of May, 1997

*Attest:*

BRUCE LEHMAN

*Attesting Officer*     *Commissioner of Patents and Trademarks*